United States Patent
Wan et al.

(10) Patent No.: US 8,517,600 B2
(45) Date of Patent: Aug. 27, 2013

(54) DEPOSITION SENSOR BASED ON DIFFERENTIAL HEAT TRANSFER RESISTANCE

(75) Inventors: Zhaoyang Wan, Yardley, PA (US); Caibin Xiao, Holliston, MA (US)

(73) Assignee: General Electric Company, Schenectady, NY (US)

( * ) Notice: Subject to any disclaimer, the term of this patent is extended or adjusted under 35 U.S.C. 154(b) by 718 days.

(21) Appl. No.: 12/606,325

(22) Filed: Oct. 27, 2009

(65) Prior Publication Data

US 2011/0096807 A1 Apr. 28, 2011

(51) Int. Cl.
*G01N 25/20* (2006.01)
*G01K 17/00* (2006.01)
*G01K 3/00* (2006.01)
*G01K 7/00* (2006.01)

(52) U.S. Cl.
USPC ............... 374/7; 374/29; 374/43; 374/110; 374/166

(58) Field of Classification Search
USPC .................. 374/7, 29, 43, 110, 166
See application file for complete search history.

(56) References Cited

U.S. PATENT DOCUMENTS

| | | | |
|---|---|---|---|
| 3,733,887 A | 5/1973 | Stanley et al. | |
| 3,834,873 A | 9/1974 | Picker | |
| 4,138,878 A | 2/1979 | Holmes et al. | |
| 4,383,438 A | 5/1983 | Eaton | |
| 4,408,568 A | 10/1983 | Wynnyckyj et al. | |
| 4,571,094 A | 2/1986 | Wynnyckyj et al. | |
| 4,577,976 A * | 3/1986 | Hayashi et al. | 374/29 |
| 4,595,297 A | 6/1986 | Liu et al. | |
| 4,607,961 A | 8/1986 | Wynnyckyj et al. | |
| 4,722,610 A | 2/1988 | Levert et al. | |
| 4,729,667 A | 3/1988 | Blangetti et al. | |
| 4,779,994 A | 10/1988 | Diller et al. | |
| 4,812,050 A * | 3/1989 | Epstein et al. | 374/1 |
| 4,910,999 A | 3/1990 | Eaton | |

(Continued)

FOREIGN PATENT DOCUMENTS

WO 0005572 A1 2/2000

OTHER PUBLICATIONS

Jones et al.,"The Use of a heat Flux Sensor in Monitoring Fouling", Conference Proceedings European Commission , Science Research, pp. 230-241, Mar. 23, 1994.

(Continued)

*Primary Examiner* — Mirellys Jagan
(74) *Attorney, Agent, or Firm* — Wegman, Hessler & Vanderburg

(57) ABSTRACT

A system and method are disclosed wherein differential heat transfer resistances are used to effectively and efficiently detect the early onset of deposit accumulation in industrial fluid processes and fluid transport vehicles.

According to one embodiment, a probe is provided in conjunction with a heat source, a water source and a probe. The probe is comprised of a heat transfer surface, a first part of which is covered only by a thin metal layer. The second or remaining portion of the heat transfer surface is covered by a heat flux sensor and a thin metal layer. The metal layers of both the first and second areas of the probe are connected, and water flows across the full heat transfer surface. Deposition forms on a portion of the heat transfer surface as a result of slow water flow and elevated water temperature. The temperatures of the heat source, water source, and heat flux are measured. The deposition rate as a rate of change of heat transfer resistance is measured.

3 Claims, 3 Drawing Sheets

(56) References Cited

U.S. PATENT DOCUMENTS

| | | | |
|---|---|---|---|
| RE33,346 E | 9/1990 | Knudsen et al. | |
| 5,171,518 A | 12/1992 | Barshay et al. | |
| 5,314,247 A * | 5/1994 | Liebert et al. | 374/29 |
| 5,429,178 A | 7/1995 | Garey et al. | |
| 5,590,706 A | 1/1997 | Tsou et al. | |
| 5,816,706 A * | 10/1998 | Heikkila et al. | 374/134 |
| 5,855,791 A | 1/1999 | Hays et al. | |
| 6,062,069 A | 5/2000 | Panchal et al. | |
| 6,219,573 B1 | 4/2001 | Pompei | |
| 6,238,085 B1 | 5/2001 | Higashi et al. | |
| 6,241,383 B1 | 6/2001 | Feller et al. | |
| 6,264,362 B1 | 7/2001 | Rolston | |
| 6,390,669 B1 | 5/2002 | Nakamura et al. | |
| 6,499,876 B1 * | 12/2002 | Baginksi et al. | 374/7 |
| 6,508,585 B2 | 1/2003 | Nakamura et al. | |
| 6,575,662 B2 | 6/2003 | French | |
| 7,077,563 B2 | 7/2006 | Xiao et al. | |
| 2005/0105584 A1 | 5/2005 | Ichikawa et al. | |
| 2006/0032606 A1 | 2/2006 | Thybo et al. | |
| 2009/0262777 A1 | 10/2009 | Sakami et al. | |

OTHER PUBLICATIONS

PCT/US2010/051061, International Search Report and Written Opinion, Dec. 28, 2010.

* cited by examiner

DEPOSITION SENSOR BASED ON DIFFERENTIAL HEAT TRANSFER RESISTANCE

FIELD OF THE INVENTION

This invention is related to monitoring mineral and biofilm deposition in industrial systems. With more particularity, the invention relates to a means and a method for monitoring and measuring mineral and biofilm depositions on equipment in industrial fluid processing systems.

BACKGROUND OF THE INVENTION

Chemical and/or biological deposition in industrial fluid processes adversely affects processing efficiency and can adversely impact manufacturing processes, including operational downtime and potentially even plant shutdown. It is understood within the art that mineral and/or biofilm deposition in cooling towers, heat exchangers and other fluid processing vessels reduces critical heat transfer efficiency, decreases flow velocity and can potentially lead to structure fatigue and crack formation. Additionally, the maintenance of service water heat exchanger performance is a safety issue for utility plants, especially nuclear power plants.

The onset of mineral and/or biological deposits in industrial fluid processes has been monitored by measuring either the temperature difference across a heat transfer surface or by measuring physical and chemical changes caused by deposition on a clean surface immersed in the fluid by way of electrochemical, optical, spectroscopic or acoustic methods. Several monitoring systems based on temperature measurement are known and have been used to monitor mineral and biofilm deposition, particularly in heat exchangers and cooling towers. The heat transfer surface in many of these systems is easy to set up and operate. Heat transfer resistance values are provided for the simulated heat transfer surface, which can be correlated to, for example, the overall heat transfer efficiency of heat exchangers. However, deposit monitoring based on temperature measurement is subject to process variations such as changes in process temperature, flow velocity and environmental temperature. For example, changes in power supply to an electric heater in a side stream heat flux simulator can cause errors. Unfortunately, because of the effect of process variables, many commercially available deposit monitoring systems lack the sensitivity required to detect the early onset of deposit accumulation. Consequently, detecting the early onset of deposit accumulation in a cost effective manner has heretofore been difficult to achieve.

Methods used to measure the physical and chemical changes caused by deposition include optical transmittance, fluorescence, and quartz crystal microbalance. The sensitivity of these methods is usually high. However, these methods require relatively expensive instruments. Variations and process parameters affect the measurements, and a heat transfer surface may not be easily incorporated.

In U.S. Pat. No. 4,326,164 a probe for monitoring the corrosion caused by a corrosive medium is provided. The probe comprises a first corrodible resistance element, a second corrodible resistance element having a temperature resistance characteristic similar to that of the first element, each element being in the shape of a rectangular prism, the thickness of the second element being greater than that of the first element.

U.S. Pat. No. 7,077,563 discloses and claims a method for the measurement of differential heat flux, comprising the steps of (a) providing a heat transfer reference surface; (b) providing a heat transfer fouling surface; (c) providing a heat transfer path capable of transferring heat flux between the reference surface and the fouling surface; (d) providing a pair of heat flux sensors, one sensors connected to the reference surface and the other sensor connected to the fouling surface; (e) measuring heat flux values directly from each sensor without having to measure temperature difference between the sensors; (f) calculating differential heat flux data across the heat transfer path from the heat flux values; (g) utilizing the differential heat flux data to detect and quantify deposit accumulation at the fouling surface; and wherein the heat flux values at the reference surface and the fouling surface both change in response to deposit accumulation at the fouling surface.

A disadvantage of the above apparatus and method is the difficulty of establishing a clean heat transfer surface in the same fluid as the heat transfer surface for detection.

Another problem to be overcome is that differential heat flux measurement is subject to flow rate variation. For example, fouling resistance on an active or "in use" detection surface is 5 versus 0 for the clean reference surface. Flow convective heat transfer resistance is 5 for both surfaces. The total heat transfer resistances are 10 for the active detection surface and 5 for the clean surface, a ratio of 2:1. If convective heat transfer resistance changes from 5 to 1 due to flow rate increase, and the total heat transfer resistances are 6 for the detection surface versus 1 for the clean surface, then what results is a ratio of 6:1. With total resistance ratio changing between the two surfaces, the differential heat flux will change, yet not as a result of fouling.

Accordingly, a need exists for an improved system for the monitoring and measurement of deposit accumulation in industrial fluid processes and fluid transport vessels, which is not negatively affected by flow rate. It is desirable to have a fast, accurate and cost-effective system that is able to detect and measure the early onset of chemical and/or biological deposition, while relatively insensitive to process variations such as changes in process temperature, flow velocity and environmental temperature.

SUMMARY OF THE INVENTION

A system and method are disclosed wherein differential heat transfer resistances are used to effectively and efficiently detect the early onset of deposit accumulation in industrial fluid processes and fluid transport vehicles.

According to one embodiment, a probe is provided in conjunction with a heat source, a water source and a probe. The probe is comprised of a heat transfer surface, a first part of which is covered only by a thin metal layer. The second or remaining portion of the heat transfer surface is covered by a heat flux sensor and a thin metal layer. The metal layers of both the first and second areas of the probe are connected, and water flows across the full heat transfer surface. Deposition forms on a portion of the heat transfer surface as a result of slow water flow and elevated water temperature. The temperatures of the heat source, water source, and heat flux are measured. The deposition rate as a rate of change of heat transfer resistance is measured.

A further embodiment provides a system that comprises two probes, wherein each probe is comprised of a heat transfer surface, a first part of each probe is covered only by a thin metal layer and the second portion of the heat transfer surface of each probe is covered by a heat flux sensor and a thin metal layer, and further wherein one probe has a low power supply heat source, the other probe has a high power supply heat source. In this embodiment the deposition rate may be calculated as the rate of change of differential heat transfer resistance.

A further embodiment provides for a system comprising a probe, one heat source and one water source. In this embodiment, the probe is comprised of a heat transfer surface, wherein the entire heat transfer surface is covered by heat flux sensor and thin metal layer. Water flows across the heat transfer surface, and temperatures of the heat source, water source and heat flux are measured. Thereafter, deposition rate is calculated as rate of change of heat transfer resistance.

One embodiment provides a system that comprises two probes wherein the entire heat transfer surface of both probes is covered by a heat flux sensor and a thin metal layer, wherein one probe comprises a low power supply heat source, and the other probe comprises a high power supply heat source. In this embodiment, the deposition rate is calculated as rate of change of differential heat transfer resistance.

The various features of novelty which characterize the invention are pointed out with particularity in the claims annexed to and forming a part of this disclosure. For a better understanding of the invention, its operating advantages and benefits obtained by its uses, reference is made to the accompanying drawings and descriptive matter. The accompanying drawings are intended to show examples of the many forms of the invention. The drawings are not intended as showing the limits of all of the ways the invention can be made and used. Changes to and substitutions of the various components of the invention can of course be made. The invention resides as well in sub-combinations and sub-systems of the elements described, and in methods of using them.

DETAILED DESCRIPTION OF THE INVENTION

The singular forms "a," "an" and "the" include plural referents unless the context clearly dictates otherwise.

The modifier "about" used in connection with a quantity is inclusive of the stated value and has the meaning dictated by the context (e.g., includes the degree of error associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

A system and method are disclosed wherein differential heat transfer resistances used to effectively and efficiently detect the early onset of mineral and/or biological deposit accumulation in industrial fluid processes and fluid transport vehicles. When deposits begin to accumulate inside the fluid or a vessel under inspection, changes in heat transfer resistance occur. Since deposit accumulation leads to a change in the heat transfer resistance of the pertinent heat transfer surface, it is possible to detect the onset of deposit accumulation by measuring differential changes in heat transfer resistances that occur between the respective heat transfer surfaces.

Figure 1:
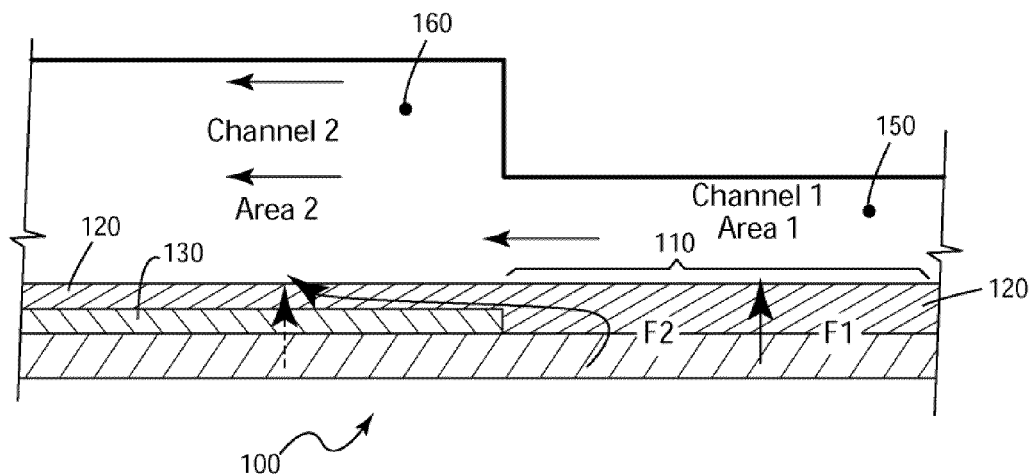
FIG. 1 is a perspective view of a deposition sensor system in accordance with one embodiment of the invention.

According to one embodiment, a probe is provided in conjunction with a heat source, a water source and a probe. In this embodiment, the probe is comprised of a heat transfer surface, a first part of which is covered only by a thin metal layer. The second and remaining portion of the heat transfer surface is covered by a heat flux sensor and a thin metal layer. The metal layers of both areas are connected, and water flows across the full heat transfer surface. As seen by example with the probe 100 in FIG. 1, a first portion of the heat transfer surface 110 is covered only by thin metal layer 120, the second portion of the heat transfer surface 110 is covered by heat flux sensor 130 and a thin metal layer 120. The thin metal layer 120 is connected across the entire probe. Water flows across the probe, from a small cross-section area 150, where it contacts the area of the first part of the probe 100 wherein the heat transfer surface 110 is covered by a thin metal layer 120, and continues on to a larger cross-section area 160 where it contacts the heat transfer surface 110 of the probe that is covered by a heat flux sensor 130 and a thin metal layer 120. Deposition forms on the section of the probe 100 covered by a heat flux sensor 130 and a thin metal layer 120 due to slow flow and elevated water temperature.

In order to determine the deposition formation, the temperatures of a heat source ($T_h$) and water source ($T_w$), and heat flux via the heat flux sensor 130 ($F_2$) are measured. The deposition rate may then be calculated as the rate of change of heat transfer resistance expressed as $(T_h-T_w)/F_2$.

In a further embodiment, the system is comprised of two probes, wherein one probe has a low power supply heat source, the other probe has a high power supply heat source. In this embodiment, it is possible to calculate the deposition rate as rate of change of differential heat transfer resistance $(T_{h\_h}-T_{w\_h})/F_{2\_h}-(T_{h\_l}-T_{w\_l})/F_{2\_l}$.

An alternate embodiment comprises a probe, one heat source and one water source. In this embodiment, the entire heat transfer surface of a probe is covered by a heat flux sensor and thin metal layer, so that the surface of the probe is consistent across the length of the heat transfer surface. Water flows from a small cross-section area to a large cross-section area along the length of the probe. Temperature measurements of the heat source ($T_h$) and water source ($T_w$), and heat flux (F) are taken. The deposition rate may then be calculated as a rate of change of heat transfer resistance expressed as $(T_h-T_w)/F$.

Figure 2:
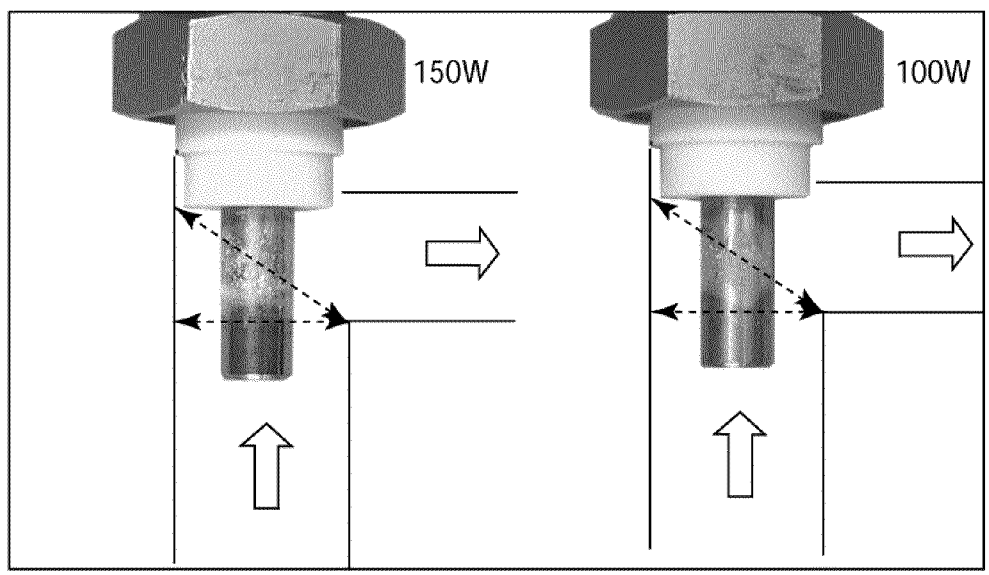
FIG. 2 is a demonstration of deposition forming at heat transfer surfaces where water flows through a large cross-section area.
Figure 3:
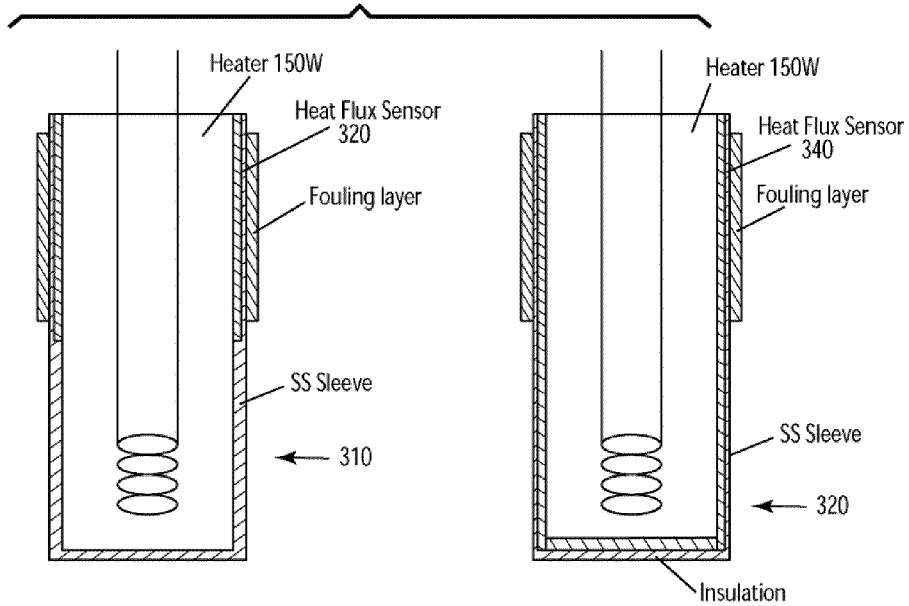
FIG. 3 is two designs of the deposition probe in accordance with embodiments of the invention.

In a further embodiment, the device is comprised of two probes, wherein one probe has a low power supply heat source, the other has a high power supply heat source. In this embodiment, the deposition rate may be calculated as a rate of change of differential heat transfer resistance $(T_{h\_h}-T_{w\_h})/F_{\_h}-(T_{h\_l}-T_{w\_l})/F_{\_l}$ FIG. 2 is a pictorial demonstration of deposition forming on the heat transfer surfaces of probes in accordance with an embodiment of the present invention. As shown, the deposition occurs where the water flows through a large cross sectional area. As for FIG. 3, it is a representation of two designs of deposition probes according to an embodiment of the present invention. The probe 310, shows an embodiment wherein a heat flux sensor 320 covers a first part or half of heat transfer area. The probe 320, depicted on the right of FIG. 3, is a depiction of a heat flux sensor 340 that covers the entire heat transfer area, as an alternate embodiment of the present invention.

Heat flux sensors are available from a number of sources, for example Omega Engineering, Inc. (Stamford, Conn.). The sensors generated an electrical signal indicative of changes in heat flux measured at the heat transfer surfaces. The sensors may be connected to a signal processing unit and display to process the corresponding electrical signal generated by the sensors. Additionally, the heat source that can be used to introduce a heat transfer surface includes, but is not limited to electric heat, sonic or electromagnetic radiation heat, and heat carrying process fluids.

Figure 4:
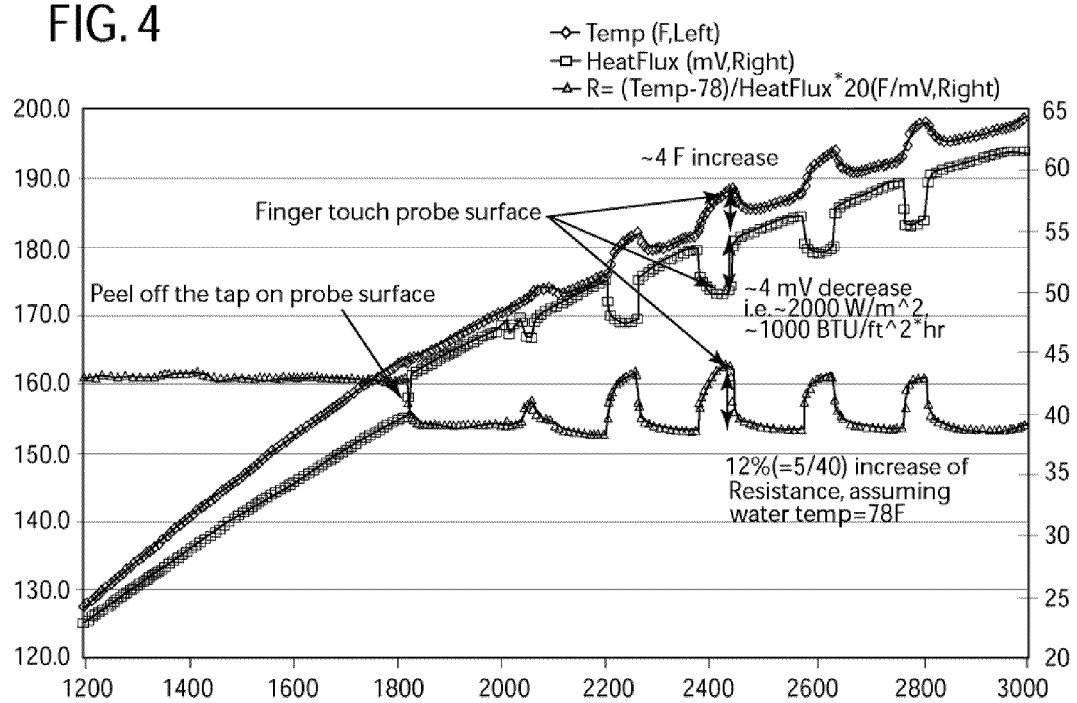
FIG. 4 is a graph demonstrating sensitivity of a probe in accordance with one embodiment of the invention.

The reason for using differential heat transfer resistance is to cancel the effect of process variations, such as changes in process temperature, flow velocity and environmental temperature, i.e. $(Th\_h-Tw\_h)/F\_h-(Th\_l-Tw\_l)/F\_=R\_convective+r\_deposit\_h-(R\_convective+r\_deposit\_l)=r\_deposit\_h-r\_deposit\_l$. As shown by FIG. 4, the environmental temperature was effected by just touching with a human finger. As demonstrated graphically in FIG. 4 each time a finger toucheed the probe heat transfer surface, there was s 4 F temp increase and a 4 mV heat flux decrease, which resulted in a 12% resistance increase. Peel off the tap on probe surface results in a 12% resistance decrease.

Figure 5:
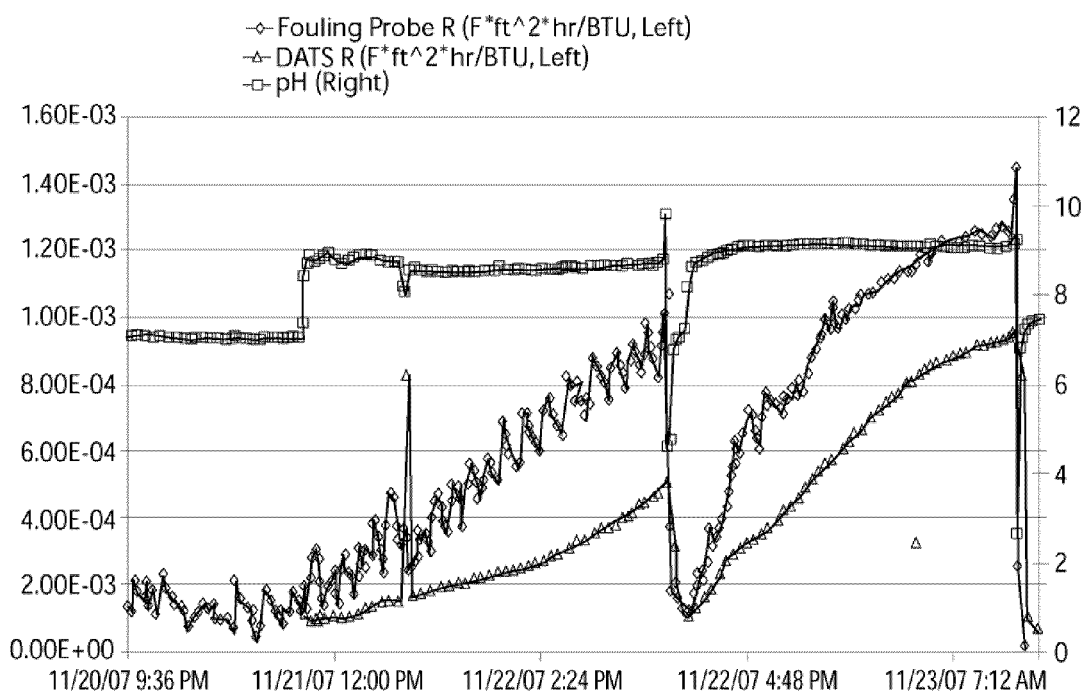
FIG. 5 shows the results of a deposition probe according to one embodiment of the invention and a commercially available Deposition Accumulation Testing System put in serial in the same cooling tower side stream.

The present invention was shown to have enhanced performance over what is currently available in the prior art. FIG. 5 demonstrates the results of a deposition probe according to one embodiment of the present invention versus a commercially available deposition accumulation testing system (DATS). Both systems were put in serial combination in the same cooling tower side stream. It can be clearly seen that the fouling probe according to the present invention is more sensitive and shows higher responses than DATS.

While the present invention has been described with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but all that fall within the scope of the appended claims.

What is claimed is:

1. A system for measuring deposition rate comprising a probe having:
    i) a heat transfer surface defining a first portion and a second portion;
    ii) a heat flux sensor covering said second portion of the heat transfer surface;
    iii) a thin metal layer covering said heat flux sensor and said first portion of said heat transfer surface;
    iv) a heat source operatively associated with said probe and adapted to supply heat to said heat transfer surface;
    v) a water source operatively associated with said probe and adapted to provide a flow of water along said heat transfer surface, wherein water flows from a small cross-sectional area contacting the first portion of the heat transfer surface to a larger cross sectional area contacting the second portion of the heat transfer surface, said probe being configured to measure the temperature of the heat source (Th), the temperature of the water source (Tw), and the heat flux at the larger cross sectional area (F2) and calculating the deposition rate as the rate of change of heat transfer resistance expressed according to the formula $(Th)-(Tw)/(F2)$.

2. The system of claim 1 comprising two probes, wherein one probe has a low power supply heat source and the other has a high power supply heat source.

3. The system of claim 2 wherein the deposition rate is calculated as a rate of change of differential heat transfer resistance according to the formula:

$$(Th\_h-Tw\_h)/F\_h-(Th\_l-Tw\_l)/F\_l$$

wherein Th_h is the temperature of the heat source of a first of the two probes, Tw_h is the temperature of the water source of the first of the two probes, and F_h is the heat flux of the first of the two probes, Th_l is the temperature of the heat source of a second of the two probes, Tw_l is the temperature of the water source of the second of the two probes, and $F\_{-1}$ is the heat flux of the second of two probes.

* * * * *